(12) United States Patent
Fiala

(10) Patent No.: US 7,771,957 B2
(45) Date of Patent: Aug. 10, 2010

(54) METHOD FOR DIAGNOSING ALZHEIMER'S DISEASE

(75) Inventor: Milan Fiala, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 95 days.

(21) Appl. No.: 11/875,729

(22) Filed: Oct. 19, 2007

(65) Prior Publication Data

US 2009/0104629 A1    Apr. 23, 2009

(51) Int. Cl.
*G01N 33/567* (2006.01)
*G01N 33/53* (2006.01)
*G01N 33/566* (2006.01)
*G01N 33/48* (2006.01)
*C12Q 1/00* (2006.01)

(52) U.S. Cl. ............... 435/7.21; 435/4; 435/7.1; 435/7.8; 436/501; 436/63

(58) Field of Classification Search .............. None
See application file for complete search history.

(56) References Cited

OTHER PUBLICATIONS

Fiala et al., 2005, J. Alzheimer Dis. 7, pp. 221-232.*
Fiala, M. et al. 2007 "Phagocytosis of amyloid-β and inflammation: Two faces of innate immunity in Alzheimer's Disease" *J Alzheimer's Dis* 11:457-463.
Fiala, M. et al. 2007 "Innate immunity and transcription of MGAT-III and Toll-like receptors in Alzheimer's disease patients are improved by bisdemethoxycurcumin" *Proc Natl Acad Sci USA* 104:12849-12854.
Zhang, L. et al. 2006 "Curcuminoids enhance amyloid-β uptake by macrophages of Alzheimer's disease patients" *J Alzheimer's Dis* 10:1-7.
International Search report mailed on Jul. 28, 2008, for International Application No. PCT/US07/81989 filed on Oct. 19, 2007, 3 pages.
Maggio, J.E. et al., "Reversible in vitro growth of Alzheimer disease β-amyloid plaques by deposition of labeled amyloid peptide," *Proc. Natl. Acad. Sci. USA*, Jun. 1992, vol. 89, pp. 5462-5466.
Venkitaramani, D.V. et al., "β-Amyloid Modulation of Synaptic Transmission and Plasticity," *The Journal of Neuroscience*, Oct. 31, 2007, vol. 27, No. 44, pp. 11832-11837.

* cited by examiner

*Primary Examiner*—Olga N Chemyshev
(74) *Attorney, Agent, or Firm*—Townsend and Townsend and Crew LLP

(57) ABSTRACT

The invention relates to method of diagnosing Alzheimer's disease or detecting a predisposition to Alzheimer's disease including providing a test cell sample from a subject, exposing the test cell sample to labeled amyloid beta peptides, and determining the level of labeled amyloid beta peptides in the test cell sample, wherein lower levels of labeled amyloid beta peptides in the test cell sample compared to a control cell sample are indicative of Alzheimer's disease.

16 Claims, 9 Drawing Sheets

Uptake of FITC-Aβ by monocytes

| Control Subject | Mean Aβ uptake* | AD Patient | Mean Aβ uptake* |
|---|---|---|---|
| 1 | 7020 | 1 | 517 |
| 2 | 2893 | 2 | 353 |
| 3 | 1061 | 3 | 107 |
| 4 | 1404 | 4 | 449 |
| 5 | 3259 | 5 | 4406 |
| 6 | 5953 | 6 | 708 |
| 7 | 1369 | 7 | 235 |
| 8 | 3666 | 8 | 4442 |
| 9 | 4608 | 9 | 5153 |
| 10 | 3460 | 10 | 234 |
|  |  | 11 | 228 |
|  |  | 12 | 285 |

*Events in UR (FL1= FITC-Aβ, FL2= PE-CD14)

Fluorescence microscopy

Control subjects

AD patients

Uptake of FITC-Aβ by CD44-positive cell

Uptake of FITC-Aβ by monocytes

Control  AD

IOD per monocyte

Flow cytometry

Uptake of FITC-Aβ by CD44-positive cell

CD44 per cell

| Image | Area | Density | IOD | Cells | Category | Patient# | Sex | Age |
|---|---|---|---|---|---|---|---|---|
| #13 A 100X-1 | 377.9481667 | 13.06445 | 16215.29 | 3 | AD | A | Female | 74 |
| #13 A 100X-2 | 64.18614857 | 8.726474 | 3581.213 | 7 | AD | A | Female | 74 |
| #13 A 100X-3 | 103.2189533 | 7.243701 | 4623.122 | 6 | AD | A | Female | 74 |
| #13 A 100X-4 | 267.076935 | 23.95417 | 14669.32 | 2 | AD | A | Female | 74 |
| #24 B 100X-1 | 163.763636 | 11.30034 | 13065.63 | 5 | AD | B | Female | 73 |
| #24 B 100X-2 | 300.767855 | 27.75219 | 17065.7 | 2 | AD | B | Female | 73 |
| #29 B 100X-2 | 423.44232 | 27.87319 | 21679.97 | 2 | AD | B | Female | 73 |
| #29 B 100X-3 | 176.315795 | 32.93639 | 12799.81 | 2 | AD | B | Female | 73 |
| #29 B 100X-4 | 170.71428 | 61.75754 | 11611.61 | 1 | AD | B | Female | 73 |
| #29 B 100X-5 | 719.95831 | 53.64225 | 48179.87 | 1 | AD | B | Female | 73 |
| #29 B 100X-6 | 137.1702167 | 18.25119 | 7956.163 | 3 | AD | B | Female | 73 |
| Averages | | | 15586.15 | | | | | |
| SEM | | | 3817.652 | | | | | |
| #1 C 100X-1 | 1771.875 | 27.26303 | 152071.7 | 3 | Control | C | Male | 72 |
| #1 C 100X-2 | 855.4211 | 13.26114 | 65778.38 | 5 | Control | C | Male | 72 |
| #1 C 100X-3 | 954.352975 | 19.08382 | 86495.7 | 4 | Control | C | Male | 72 |
| #13 C 100X-1 | 336.62097 | 33.91714 | 23281.89 | 2 | Control | C | Male | 72 |
| #13 C 100X-2 | 322.25 | 9.779048 | 12098.77 | 3 | Control | C | Male | 72 |
| #13 C 100X-3 | 1007.953467 | 12.6433 | 61608.25 | 3 | Control | C | Male | 72 |
| #13 C 100X-4 | 266.7149778 | 6.288684 | 17255.62 | 9 | Control | C | Male | 72 |
| #13 C 100X-5 | 8178.5557 | 52.37997 | 538682.7 | 1 | Control | C | Male | 72 |
| #11 D 100X-1 | 6261.643 | 33.64436 | 443005.5 | 2 | Control | D | Male | 72 |
| #11 D 100X-2 | 1687.242367 | 16.47125 | 107577.3 | 3 | Control | D | Male | 72 |
| #11 D 100X-3 | 1346.051525 | 15.2071 | 100412.5 | 4 | Control | D | Male | 72 |
| Averages | | | 119659.1 | | | | | |
| SEM | | | 15655.63 | | | | | |

*FIG. 6A*

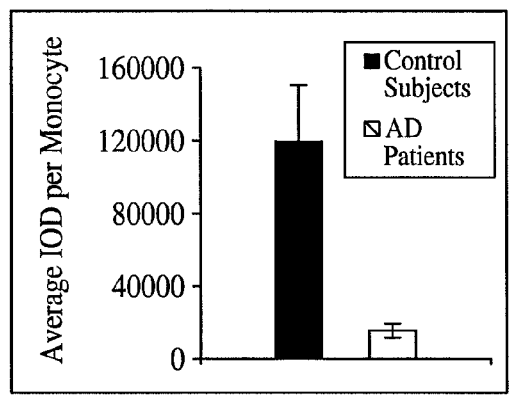

*FIG. 6B*

SEQUENCE LISTING

```
<160> NUMBER OF SEQ ID NOS: 2

<210> SEQ ID NO 1
<211> LENGTH: 40
<212> TYPE: PRT
<213> ORGANISM: Homo sapien

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Homo sapien

<400> SEQUENCE: 2
```

-continued

```
Asp Ala Glu Phe Arg His Asp Ser Gly Tyr Glu Val His His Gln Lys
 1               5                  10                 15

Leu Val Phe Phe Ala Glu Asp Val Gly Ser Asn Lys Gly Ala Ile Ile
                20                  25                 30

Gly Leu Met Val Gly Gly Val Val Ile Ala
             35              40
```

METHOD FOR DIAGNOSING ALZHEIMER'S DISEASE

BACKGROUND OF THE INVENTION

1. Field of the Invention

In preferred embodiments, the present invention relate, to use of a biomarker of Alzheimer's disease for diagnostic tests as well as screening assays for agents that may be useful in treating Alzheimer's disease.

2. Description of the Related Art

The search for Alzheimer's disease (AD) biomarkers in body fluids began with measurements of pathogenic molecules, amyloid-β (Aβ) 1-40 and 1-42, in cerebrospinal fluid (CSF) (Blennow K & Hampel H. 2003 *Lancet Neurol* 2:605-613; Colton C A et al. 2006. *J Neuroinflammation* 3:27) and plasma, and the search for various markers has continued into genomics, proteomics and metabolomics (Abdi et al. 2006. *J Alzheimers Dis* 9:293-348.) CSF proteome in Alzheimer's disease has been characterized by several groups and diagnostic utility of a roster of proteins has been shown (reviewed in (Abdi et al., supra)). Plasma proteome shows changes in multiple proteins implicated in the disease pathology, in particular inflammation, but the test is only 56% sensitive and 80% specific (Hye el al. 2006. *Brain* 129:3042-3050).

CSF- and blood-based tests are gaining entry into clinical use. Low CSF level of Aβ$_{1-42}$ and a high phosphorylated-τ and total τ levels are widely used in Europe to differentiate mild cognitive impairment (MCI) and early AD from normal aging, depression and alcohol abuse (Blennow K & Hampel H. 2003 *Lancet Neurol* 2:605-613.). Blood tests are more suitable than CSF tests for screening use. The association of plasma Aβ$_{1-40}$ and Aβ$_{1-42}$ levels with dementia has been evaluated in several longitudinal studies (Motter et al 1995. *Ann Neurol* 38:643-648.; Motter et al. 1995. *Ann Neurol* 38:643-648; Pomara et al. 2005. *Am J Geriatr Psychiatry* 13:914-917). The result of a high plasma concentration of Aβ$_{1-40}$ and a low concentration of Aβ$_{1-42}$ baseline has been the strongest predictors of dementia in a recent longitudinal study (van Oijen et al. 2006. *Lancet Neurol* 5:655-660).

Other proposed biomarkers include inflammatory molecules (C1q, interleukin-1 and interleukin-6, transforming growth factor-β, tumor necrosis factor-α, and α-1-chymotrypsin (Mrak and Griffin 2005 *J Alzheimers Dis* 8:369-375; Mrak and Griffin 2005. *J Alzheimers Dis* 8:369-375). The presence of inflammatory molecules in body fluids reflects the inflammatory component of AD. Divergent results of inflammatory markers in different studies have been explained by the presence of peripheral immune suppression associated with central neuroinflammatory processes (Mrak and Griffin 2005 *J Alzheimers Dis* 8:369-375).

Brain amyloidosis of sporadic AD has been attributed to defective Aβ clearance (Motter et al. 1995. *Ann Neurol* 38:643-648). Peripheral clearance of Aβ by complement C3-adherence to erythrocytes is lower in Alzheimer's disease patients compared to control subjects (Rogers et al. 2006. *Neurobiol Aging* 27:1733-1739). We have searched for peripheral biomarkers of AD based on the presence of defective phagocytosis of Aβ in patients with sporadic Alzheimer's disease. Macrophages of patients with sporadic Alzheimer's disease generally show defective phagocytosis of Aβ in spite of apparently normal phagocytosis of bacteria, whereas macrophages of a majority of age-matched, cognitively normal persons perform excellent phagocytosis of Aβ (Fiala et al. 2005. *J Alzheimers Dis* 7:221-232; discussion 255-262). Surprisingly, as shown herein, monocytes freshly isolated from peripheral blood mononuclear cells: (PBMC's) also show robust differences between patients and controls in their interactions with FITC-Aβ. In addition, during phagocytosis of Aβ, control monocytes express several molecules that may serve as biomarkers; in contrast, Alzheimer's disease monocytes are susceptible to apoptosis.

Amyloid-precursor protein (APP) is the precursor protein from which the pathogenic amyloid-beta is cut out. APP is expressed from a single gene in a wide variety of tissue and cell types. At least ten isoforms of the protein have been described, derived by alternative splicing; the 695, 751 and 770 amino acid isoforms appear to be most common. APP695 is exclusive to neurons while the other forms are present in many cell types. The protein has a transmembrane region near the c-terminus, undergoes O-linked and N-linked glycosylation, and contains a Kunitz-type protease inhibitor (KPI) domain in its c-terminal portion"

Sequential proteolytic processing of APP (the 770 amino acid isoform) by β- and γ-secretase after amino acids 671 and 711/713/714, respectively, give rise to the Aβ peptides. The Aβ peptides, known as Aβ x-40, x-42 and x-43 for the number of amino acids they contain, are deposited into the hallmark amyloid plaques of AD. It is these peptides, especially Aβ x-42 and x43, that are thought to be causal in AD.

SEQUENCE LISTING TABLE

| PEPTIDE | SEQUENCE | SEQ ID NO |
|---|---|---|
| Amyloid beta 1-40 | H-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-OH | 1 |
| Amyloid beta 1-42 | H-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-OH | 2 |

SUMMARY OF THE INVENTION

A method is disclosed in accordance with an embodiment of the present invention for diagnosing Alzheimer's disease. The method comprises: providing a test cell sample from a patient; exposing the test cell sample to a labeled amyloid beta polypeptide; and determining an intracellular level of the labeled amyloid beta polypeptide in the test cell sample, wherein a lower level of labeled amyloid beta polypeptide in the test cell sample compared to a control cell sample is indicative of Alzheimer's disease.

In one preferred embodiment of the method, the test and control cell samples are macrophages. In preferred embodiments, the labeled amyloid beta polypeptide is a full-length amyloid precursor protein, a peptide fragment thereof, including in particular Aβ$_{1-40}$ and Aβ$_{1-42}$ fragments (SEQ ID NO: 1 and SEQ ID NO: 2). The test cell sample may be exposed to the labeled amyloid beta polypeptide in a cell culture media. The labeled amyloid beta polypeptide is preferably fluorescently labeled, e.g., FITC, but in one embodiment, the labeled amyloid beta polypeptide is radiolabeled. In another embodiment, the labeled amyloid beta polypeptide is chromatogenically labeled.

The level of labeled amyloid beta polypeptide may be determined by fluorescence microscopy imaging. Alternatively, the level of labeled amyloid beta polypeptide may be determined by flow cytometry. In other embodiments, the level of labeled amyloid beta polypeptide may be determined by radioassay or chromogenic or absorbance based assays, or scintillation counting (for example with 14C-labeled amyloid beta) or by use of fluorogenic labeling.

A kit for the diagnosis of Alzheimer's disease is disclosed in accordance with another embodiment of the invention. The kit comprises: a labeled amyloid beta polypeptide; and instructions for isolating and using cell samples for determining relative levels of amyloid beta polypeptide uptake. Preferably, the amyloid beta polypeptide is labeled with a fluorescent dye, e.g., FITC. The kit may further comprise a chamber slide.

A method for detecting a predisposition to Alzheimer's disease in a subject is disclosed in accordance with another embodiment of the invention. The method comprises: providing a test cell sample from the subject; exposing the test cell sample to a fluorescently labeled amyloid beta polypeptide; and observing a pattern of cellular distribution of fluorescence, wherein an abnormal pattern of fluorescently labeled amyloid beta polypeptide in the test cell sample compared to a control sample is indicative of a predisposition to Alzheimer's disease.

A screening method for identifying a substance useful for treating and/or preventing Alzheimer's disease is disclosed in accordance with another aspect of the invention. The screening method, comprises: contacting a cell sample with the substance; contacting the cell sample with a labeled amyloid beta polypeptide; and determining if the substance effects the level of labeled amyloid beta polypeptide in the sample. In one embodiment, macrophages in 8-well chambers or multiwell (96-) well chambers are treated with the test substances at appropriate concentration for specified time and phagocytosis assay with fluorescent amyloid-beta is done by the standard technique.

In another variation to the invention, a method of diagnosing Alzheimer's disease in a subject is disclosed. The method comprises: providing a test cell sample from the subject; exposing the test cell sample to an amyloid beta polypeptide; labeling the amyloid beta polypeptide by binding a labeled antibody or fragment thereof to the amyloid beta polypeptide; mid determining the level of the labeled amyloid beta polypeptide in the test cell sample, wherein lower levels of labeled amyloid beta polypeptide in the test cell sample compared to a control cell sample are indicative of Alzheimer's disease.

BRIEF DESCRIPTION OF THE DRAWINGS

FIG. 6. Localization in CD44 cells. CD44 expression for two AD patients and two controls.

DETAILED DESCRIPTION OF THE PREFERRED EMBODIMENT

Part 1

Figures 1A, 1B:
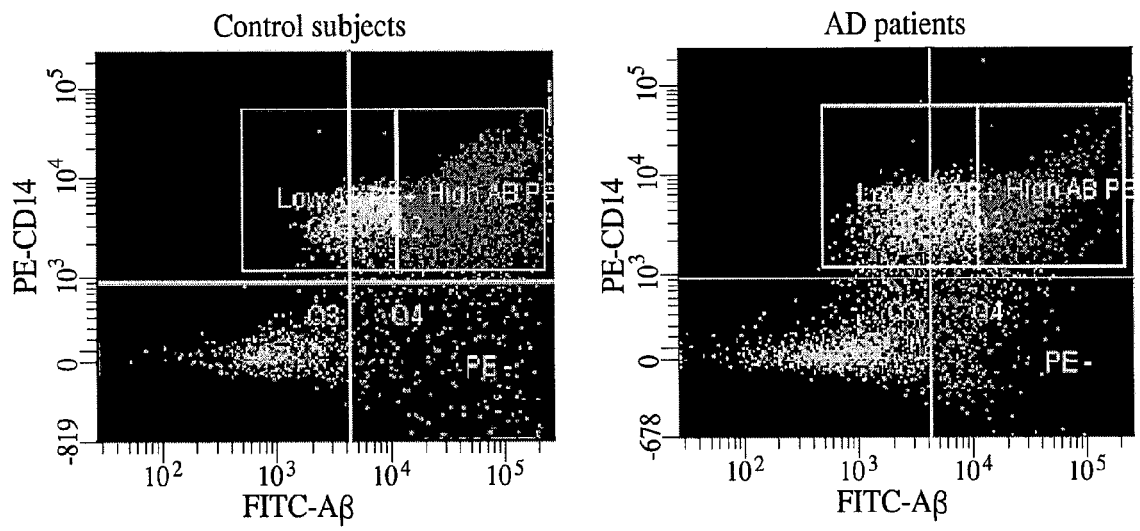
FIG. 1. Flow cytometry of Aβ phagocytosis by monocytes: high intracellular uptake by control monocytes. (A) Uptake of Aβ by monocytes measured by FACScan analytic flow cytometry. Monocytes of 10 control subjects and 12 AD patients were incubated with FITC-Aβ (2 µg/ml), stained with PE-anti-CD14 and analyzed for signal in upper right (UR) quadrant (P=0.020 by Mann-Whitney t-test). (B) Monocytes with a high Aβ uptake were sorted by FACS Vantage SE sorting flow cytometer into high Aβ uptake and low Aβ uptake CD14-positive monocytes. (C) Fluorescence microscopy of high Aβ uptake monocytes. Control monocytes show intracellular fluorescence; AD monocytes show surface staining.

Innate immune cells have crucial role in maintaining the pristine milieu of the nervous system; however, their function in the clearance of amyloid-β (Aβ) is defective in some patients with sporadic Alzheimer disease (AD). We tested by flow cytometry or fluorescence microscopy phagocytosis of Aβ by peripheral blood mononuclear cells (PBMC's) in 38 patients with AD (mean age 77.2 years, MMSE 21) and 39 control subjects (mean age 69.4 years). Flow cytometry showed a significantly higher uptake of FITC-Aβ in normal subjects compared to AD patients (P<0.020), but some patients' monocytes bound Aβ on the surface, as shown by cell sorting and fluorescence microscopy. To distinguish intracellular from surface uptake, we performed fluorescence microscopy of PBMC's incubated with FITC-Aβ or with unlabeled Aβ stained by anti-Aβ/fluorescent anti-rabbit IgG and collected by cytocentrifugation. The monocytes of control subjects showed strong intracellular uptake of Aβ (P=0.001, controls vs. patients) and clustered around aggregated FITC-Aβ. The monocytes of a control subject displayed increased CD44 expression in comparison to the monocytes of a patient. The tests of Aβ phagocytosis may serve as immunologic biomarkers for AD.

Part 2

Unless defined otherwise, technical and scientific terms used herein have the same meaning as commonly understood by one of ordinary skill in the art to which this invention belongs. See, e.g., Singleton P and Sainsbury D., Dictionary of Microbiology and Molecular Biology 3rd ed., J. Wiley & Sons, Chichester, New York, 2001.

The transitional term "comprising" is synonymous with "including," "containing," or "characterized by," is inclusive or open-ended, and does not exclude additional, unrecited elements or method steps.

The transitional phrase "consisting of" excludes any element, step, or ingredient not specified in the claim, but does not exclude additional components or steps that are unrelated to the invention such as impurities ordinarily associated therewith.

The transitional phrase "consisting essentially of" limits the scope of a claim to the specified materials or steps and those that do not materially affect the basic and novel characteristic(s) of the claimed invention.

The present invention relates to methods for the diagnosis of Alzheimer's disease (AD), methods for screening for compounds that treat or prevent AD, and to methods for the treatment of AD which are based on this diagnosis. In particular, the present invention provides methods for diagnosing Alzheimer's based on the rate of uptake of Aβ in a cell sample.

Definitions

The term antibody" (or "antibodies") is used herein in the broadest sense and refers to intact molecules as well as fragments thereof, which binds specifically to an antigenic determinant, and specifically, binds to proteins identical or structurally related to the antigenic determinant which stimulated their production. Thus, antibodies are useful in assays to detect the antigen which stimulated their production. "Antibody fragments" comprise a portion of a full-length antibody, generally the antigen binding or variable region thereof. Examples of antibody fragments include Fab, Fab', F(ab')2, and Fv fragments; diabodies; linear antibodies; single-chain antibody molecules; and multi-specific antibodies formed from antibody fragments.

Monoclonal antibodies are derived front a single clone of B lymphocytes (i.e., B cells), and are generally homogeneous in structure and antigen specificity. Polyclonal antibodies originate from many different clones of antibody-producing cells, and thus are heterogeneous in their structure and epitope specificity, but all recognize the same antigen. In some embodiments, monoclonal and polyclonal antibodies are used as crude preparations, while in preferred embodiments, these antibodies are purified. For example, in some embodiments, polyclonal antibodies contained in crude antiserum are used. Also, it is intended that the term "antibody" encompass any immunoglobulin (e.g., IgG, IgM, IgA, IgB, IgD, etc.) obtained from any source (e.g., humans, rodents, non-human primates, lagomorphs, caprines, bovines, equines, ovines, etc.).

As used herein, the terms "auto-antibody" or "auto-antibodies" refer to any immunoglobulin that binds specifically to an antigen that is native to the host organism that produced the antibody (i.e., the antibody is directed against 'self' antigens). The presence of auto-antibodies is referred to herein as "autoimmunity." As used herein, the term "antigen" is used in reference to any substance that is capable of being recognized by an antibody. It is intended that this term encompass any antigen and "immunogen" (i.e., a substance which induces the formation of antibodies).

Thus, in an immunogenic reaction, antibodies are produced in response to the presence of an antigen or portion of an antigen. The terms "antigen" and "immunogen" are used to refer to an individual macromolecule or to a homogeneous or heterogeneous population of antigenic macromolecules. It is intended that the terms antigen and immunogen encompass protein molecules or portions of protein molecules, which contains one or more epitopes. The term "epitope" as used herein, refers to that fragment of a molecule that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as "epitopes" or "antigenic determinants". An antigenic determinant may compete with the intact antigen (i.e., the immunogen used to elicit the immune response) for binding to an antibody.

As used herein, the terms "antigen fragment" and "portion of an antigen" and the like refer to a portion of an antigen. Antigen fragments or portions typically range in size, from a small percentage of the entire antigen to a large percentage, but not 100%, of the antigen. In some embodiments, antigen fragments and/or portions therefrom, comprise an "epitope" recognized by an antibody, and are therefore referred to as "immunoreactive fragments", while in other embodiments these fragments and/or portions do not comprise an epitope recognized by an antibody. In addition, in some embodiments, antigen fragments and/or portions are not immunogenic, while in other embodiments the antigen fragments and/or portions are immunogenic.

As used herein, the terms "peptide," "polypeptide" and "protein" all refer to a primary sequence of amino acids that are joined by covalent "peptide linkages." In general, a peptide consists of a few amino acids, typically from 2-50 amino acids, and is shorter than a protein. The term "polypeptide" encompasses peptides and proteins. In some embodiments, the peptide, polypeptide or protein is synthetic, while in other embodiments, the peptide, polypeptide or protein is recombinant or naturally occurring.

A synthetic peptide is a peptide which is produced by artificial means in vitro (i.e., was not produced in vivo).

The term "sample" is used in its broadest sense and encompasses samples or specimens obtained from any source. As used herein, the term "sample" is used to refer to biological samples obtained from animals (including humans), and encompasses fluids, solids, tissues, and gases. In preferred embodiments of this invention, biological samples include cerebrospinal fluid (CSF), serous fluid, urine, saliva, blood, and blood products such as plasma, serum and the like. However, these examples are not to be construed as limiting the types of samples which find use with the present invention. In one preferred embodiment, the sample comprises cells and more preferably, peripheral blood mononuclear cells (PBMC) isolated by centrifugation from a subject's blood. In another embodiment, a cell sample may be obtained from blood, muscle, connective tissue, brain or nerve tissue, and epithelial tissue. A cell sample is considered essentially free of a specific cell type if less than 1 in 1000 cells of the sample are of that cell type.

The term "amyloid-β" (or "Aβ") as used herein has the standard meaning understood in the art. The full length beta amyloid precursor protein (APP) occurs in nature in several variants, up to 770 amino acids in length, with other characterized species including variants 695, 639, 574, 547, 484, 352, 327 and 305 amino acids in length. Amyloid-β polypeptides may be of various lengths, including 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 513, 614, 615, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770 amino acids in length. Aβ polypeptides are at least 80% homologous to the wild-type amyloid-β protein, or naturally occurring variants, over their length, preferably 85%, 90%, 95%, 99% or 100% homologous. In preferred embodiments, the Aβ polypeptides are 40 or 42 amino acids in length.

As used herein, the term "immunoassay" refers to any assay that uses at least one specific antibody for the detection or quantitation of an antigen. Immunoassays include, but are not limited to, Western blots, ELISAs, radio-immunoassays, and immunofluorescence assays.

The terms "Western blot," "Western immunoblot" "immunoblot" and "Western" refer to the immunological analysis of protein(s), polypeptides or peptides that have been immobilized onto a membrane support. The proteins are first resolved by polyacrylamide gel electrophoresis (i.e., SDS-PAGE) to separate the proteins, followed by transfer of the protein from the gel to a solid support, such as nitrocellulose or a nylon membrane. The immobilized proteins are then exposed to an antibody having reactivity towards an antigen of interest. The binding of the antibody (i. e., the primary antibody) is detected by use of a secondary antibody which specifically binds the primary antibody. The secondary antibody is typically conjugated to an enzyme which permits visualization of the antigen-antibody complex by the production of a colored reaction product or catalyzes a luminescent enzymatic reaction.

As used herein the term "radioassay" includes any conventional means for determining the level of radioisotope associated with a sample. Such conventional means depend on the radioisotope employed, and may include without limitation for example, use of a gamma counter, scintillation counter, X-ray film exposure, development and densitometry (e.g., Western blotting), etc.

As used herein, a "detection antibody" is an antibody which carries a means for visualization or quantitation, which is typically a conjugated enzyme moiety that typically yields a colored or fluorescent reaction product following the addition of a suitable substrate. Conjugated enzymes commonly used with detection antibodies in the ELISA include horseradish peroxidase, urease, alkaline phosphatase, glucoamylase and β-galactosidase. In certain embodiments, the detection antibody is directed against the antibody of interest. In certain embodiments, the detection antibody is directed against the polypeptide of interest. In some embodiments, the detection antibody is prepared with a label such as biotin, a fluorescent marker, or a radioisotope, and is detected and/or quantitated using this label.

The term "patient" includes human subjects that are diagnosed to suffer from Alzheimer's disease.

As used herein, the terms "Alzheimer's disease" and "AD" refer to a neurodegenerative disorder and encompass familial Alzheimer's disease and sporadic Alzheimer's disease. The term "familial Alzheimer's disease" refers to Alzheimer's disease associated with genetic factors (i.e., inheritance is demonstrated) while "sporadic Alzheimer's disease" refers to Alzheimer's disease that is not associated with prior family history of the disease. Symptoms indicative of Alzheimer's disease in human subjects typically include, but are not limited to, mild to severe dementia, progressive impairment of memory (ranging from mild forgetfulness to disorientation and severe memory loss), poor visual spatial skills, personality, changes, poor impulse control, poor judgment, distrust of others, increased stubbornness, restlessness, poor planning ability, poor decision making, and social withdrawal. In severe cases, patients lose the ability to use language and communicate, and require assistance in personal hygiene, eating and dressing, and are eventually bedridden. Hallmark pathologies within brain tissue include extracellular neuritic amyloid plaques, neurofibrillary tangles, neurofibrillary degeneration, granulovascular neuronal degeneration, synaptic loss, and extensive neuronal cell death.

The present invention now discloses that the rate of Aβ uptake in cells present in a sample of a subject is indicative for Alzheimer's disease. This finding provides tools for diagnosing Alzheimer's disease in a subject, preferably a human subject, and methods for treating the disease, which are based on these diagnostic tools.

Thus, according to one aspect, the present invention provides a method for the diagnosis of Alzheimer's disease, the method comprising: a) providing a sample from a subject; b) contacting the sample with Aβ, or a fragment thereof that is capable of being phagocytosed by a control sample, under conditions such that the Aβ or fragment thereof may be phagocytosed by a control sample; c) determining the presence of Aβ polypeptide in said sample; wherein lower levels of Aβ polypeptide in said subject's sample relative to a control sample is indicative of Alzheimer's disease.

According to one embodiment, determination of the presence of Aβ in the sample may further comprise: (i) contacting the Aβ with a detection antibody such that the detection antibody binds to said Aβ; and (ii) detecting the binding of said detecting antibody to said Aβ; wherein said lower levels of Aβ polypeptide in said subject's sample relative to a control sample is indicative of Alzheimer's disease.

The diagnostic method of the present invention can be applied to subjects who have been previously diagnosed with Alzheimer's disease, those who are suspected of having Alzheimer's disease, and those at risk of developing Alzheimer's disease. For example, patients diagnosed with dementia, in particular, those patients who were previously clinically normal, are suitable subjects. However, it is not intended that the present invention be limited to use with any particular subject types.

According to some embodiments, the subject is a human subject. According to certain embodiments, the subject is selected from the group consisting of subjects displaying pathology resulting from Alzheimer's disease, subjects suspected of displaying pathology resulting from Alzheimer's disease, and subjects at risk of displaying pathology resulting from Alzheimer's disease.

According to another embodiment, the Alzheimer's disease diagnosed using the method of the present invention is selected from the group consisting of late onset Alzheimer's disease, early onset Alzheimer's disease, familial Alzheimer's disease and sporadic Alzheimer's disease.

According to yet another aspect, the present invention provides a method of assessing efficacy of a treatment of Alzheimer's disease in a patient comprising: a) determining a baseline rate of Aβ uptake in a first sample obtained from the patient before receiving the treatment; b) determining the rate of Aβ uptake in a second sample obtained from said patient after receiving said treatment; wherein an increase in the amount of said Aβ uptake in the post-treatment sample is correlated with a positive treatment outcome.

According to another embodiment, the amount of Aβ uptake is determined in a sample obtained from a control population and in a sample obtained from a patient suffering from Alzheimer's disease and receiving a treatment, wherein a lack of significant difference between the amount of the Aβ uptake measured in a sample obtained after beginning of the treatment compared to the amount of said Aβ uptake in a sample obtained from the control population indicates a positive treatment outcome. In a variation, the amount of Aβ uptake for the control population may determined as a standard, wherein the amount of Aβ uptake in the patient's post-treatment sample could be compared with the standard in order to evaluate efficacy of treatment.

The methods of the present invention are useful for detecting early onset Alzheimer's disease and late onset Alzheimer's disease, as well as for detecting sporadic Alzheimer's disease and familial Alzheimer's disease. As used herein, the term "early-onset Alzheimer's disease" refers to Alzheimer's disease cases diagnosed as occurring before the age of 65. As used herein, the term "late-onset Alzheimer's disease" refers to Alzheimer's disease cases diagnosed as occurring after the age of 65.

According to certain embodiments, the diagnostic method of the present invention is particularly useful for monitoring a course of treatment being administered to a patient. The methods can be used to monitor both therapeutic treatment on symptomatic patients and prophylactic treatment on asymptomatic patients.

When assessing the efficiency of treating AD by the administration of an agent, the diagnostic method of the present invention requires, determining a baseline rate of Aβ uptake in a sample obtained from a patient before administering a dosage of the agent. The baseline value is then compared with a rate of Aβ uptake after the treatment. A significant change (i.e., greater than the typical margin of experimental error in repeat measurements of the same sample, expressed as one standard deviation from the mean of such measurements) in the rate of Aβ uptake indicates a positive treatment outcome. In general, patients undergoing an initial course of treatment with an agent are expected to show an increase in the response with successive dosages, which eventually reaches a plateau. Administration of agent is generally continued while the response is increasing.

Attainment of the plateau is an indicator that the administered treatment can be discontinued or reduced in dosage or frequency.

In certain embodiments, a control value (i.e., a mean and standard deviation) of rate of Aβ uptake is determined for a control population. A lack of significant difference in the antibody concentration in a sample, obtained from an AD patient relative to the value obtained in the control population indicates a positive treatment outcome.

The present invention also provides kits for the detection of the rate of Aβ uptake. According to one currently preferred embodiment, the kit is a fluorescence microscopy kit. According to one currently preferred embodiment, the kit is a flow cytometry kit. In addition, in certain embodiments, the kits are customized for various applications.

However, it is not intended that the kits of the present invention be limited to any particular format or design. According to certain embodiments, the kits of the present invention include, but are not limited to, materials for sample collection (e.g., spinal and/or vein puncture needles), tubes (e.g., sample collection tubes and reagent tubes), holders, trays, racks, dishes, plates (e.g., 96-well microtiter plates), instructions to the kit user, solutions or other chemical reagents, and samples to be used for standardization, and/or normalization, as well as positive and negative controls. In particularly preferred embodiments, reagents included in fluorescence microscopy kits specifically intended for the determination of the uptake of an Aβ polypeptide, labeled Aβ (FITC-Amyloid-β), buffers, fixatives, cell culture media, HBSS (Hanks balanced salt solution), antifungal agents (including, for example, PENSTREP (Procaine Penicillin and Dihydrostreptomycin Sulphate) and/or FUNGIZONE (Amphotericin B)), Histopaque-1077 (a solution of Ficoll-Hypaque with density of 1077 that is used to separate mononuclear cells from venous blood), Paraformaldehyde (used as 4% for fixation of cells on slides), Phalloidin-tetramethylrhodamine (a toxin that binds to cellular cytoskeletal actin and displays the cell architecture), LYSOTRACKER fluorescent acidotropic probes for labeling and tracking acidic organelles (such as lysosomes) in live cells, Antifade reagents to increase the photostability of fluorophores in mounted samples, and blocking agents (such as a 0.1% solution of bovine serum albumin).

Based on the disclosed phenomenon of elevated concentrations of anti-aldolase antibodies in a sample from a patient with Alzheimer's disease, aspects of the present invention further provide methods for the treatment of Alzheimer's disease comprising modulating the immune response of a patient towards aldolase.

Aβ, its fragments, analogs and fragment comprising an active epitope for phagocytosis can be synthesized by solid phase peptide synthesis, produced by recombinant expression system, or can be obtained from natural sources. Automatic peptide synthesizers are commercially available from numerous suppliers, for example Applied Biosystems, Foster City, Calif. Recombinant expression can be in bacteria, such as E. coli, yeast, insect cells or mammalian cells. Procedures for recombinant expression are described by Sambrook et al., Molecular Cloning: A Laboratory Manual (C.S. H.P. Press, NY 2d ed., 1989). Some forms of Aβ are also available commercially.

As described herein above, one problem in treating patients suffering from Alzheimer's disease is the inaccuracy or delay in the disease diagnosis, resulting in a sub-optimal treatment regime. Advantageously, embodiments of the present invention provide methods for the diagnosis of Alzheimer's disease and methods for treatment based on the diagnosis outcome. Accordingly, patients amenable to treatment include those diagnosed to have low levels of Aβ uptake.

Effective treatment regime depends upon many different factors, including means of administration, target site, physiological state of the patient, and other medications administered. Treatment dosages need to be titrated according to the desired outcome (induction or suppression of the immune response) to optimize safety and efficacy. The timing of treatment employment can vary significantly according to the rate of Aβ uptake in a patient's sample after the treatment.

Agents for modulating Aβ uptake can be administered by parenteral, topical, intravenous, oral, subcutaneous, intraperitoneal, intranasal or intramuscular means for prophylactic and/or therapeutic treatment. The most typical route of administration is subcutaneous although others can be equally effective. The next most common is intramuscular injection. This type of injection is most typically performed in the arm or leg muscles. Intravenous injections as well as intraperitoneal injections, intraarterial, intracranial, or intradermal injections are also contemplated.

Agents for modulating the uptake of Aβ may optionally be administered in combination with other agents that are at least partly effective in treatment of Alzheimer's disease.

In another embodiment, the diagnostic tests described herein can also be used to screen and identify substances useful for the treatment or prevention of Alzheimer's disease. According to this embodiment, substances which reverse or improve the Alzheimer's disease-associated differences described herein (i.e. back to levels found in normal cells) would be identified and selected as substances which are potentially useful for the treatment of Alzheimer's disease.

By way of example, one such method of screening therapeutic substances would involve the steps of contacting sample cells from an AD patient with a substance being screened and an Aβ polypeptide, and detecting the level of Aβ polypeptide uptake in the sample, wherein an increase in an abnormally low level of Aβ uptake associated with Alzheimer's disease cells indicates that the substance is potentially useful for the treatment or prevention of Alzheimer's disease.

In another embodiment, the sample may be contacted with an Aβ polypeptide for various periods of time prior to determining the level of uptake. Incubation with the Aβ polypeptide may range from about 0.5 to 24 hours, preferably 8, 9, 10, 11, 12, 13, 14, 15, or 16 hours.

Aβ polypeptides may be labeled by numerous methods known in the art. The peptides may be labeled with radioactive isotopes, fluorescent dyes or epitopes tags suitable for binding to detection antibodies. The radioisotope may be, for example, 3H, 14C, 32P, 35S, or 125I. Fluorescent dyes may be, for example, Fluorescein (FITC), Phycoerythrin (PE), Cy5PE, Cy7PE, Texas Red (TR), Allophycocyanin (APC), Cy5, Cy7APC, Cascade Blue. Epitope tags may include, for example, biotin, FLAG, HIS, c-MYC, HA, VSV-G, HSV, and V5.

Flow Cytometry

Flow cytometry can be used to detect multiple immunofluorescent markers simultaneously in a quantitative manner. The technique of immunofluorescent staining is well known and can be carried out according to any of a variety of protocols, such as those described in Current Protocols in Cytometiy (John Wiley & Sons, NY, N.Y., Eds. J. Paul Robinson, et a.). Generally, a biological sample, such as peripheral blood, bone marrow, lymph node tissue, cord blood, thymus tissue, tissue from a site of infection, spleen tissue, tumor tissue, and the like, is collected from a subject and cells are isolated therefrom using techniques known in the art. In one embodiment, blood is collected from a subject and any PBMC's are isolated.

After a period of incubation with labeled protein and/or a dye-conjugated antibody, the sample cells are washed with buffered saline and resuspended in buffered saline containing protein for introduction into a flow cytometer. The flow cytometer analyzes the heterogeneous cell population one cell at a time and can classify the cells based on the binding of the immunofluorescent labeled protein or monoclonal antibody and the light scattering properties of each cell (see, for example, Immunol Today 2000; 21 (8):383-90).

Fluorescence detection is: accomplished using photomultiplier tubes; the number of detectors (channels) determines the number of optical parameters the instrument can simultaneously examine while bandpass filters ensure that only the intended wavelengths are collected. Thus, flow cytometry can routinely detect multiple immunofluorescent markers in a quantitative manner and can measure other parameters such as forward light scatter (which is an indication of cell size) and right angle light scatter (which is an indication of cell granularity). Accordingly, a wide variety of cell populations can be differentiated and sorted using immunofluorescence and flow cytometry.

For example, by combining 4 colors of immunofluorescence with the physical parameters of forward light scatter (measure of cell size) and right angle light scatter (measure of cell granularity), a six dimensional data space can be generated wherein specific cell populations found in normal blood or bone marrow are restricted to small portions of the data space. As would be recognized by the skilled artisan after reviewing the specification, more or less than 4 colors of immunofluorescent markers could also be used: Excitation of fluoroflores is not limited to light in the visible spectrum; several dyes, such as the Indo series (for measuring intracellular calcium) and the Hoesch series (for cell-cycle analyses) are excitable in the ultraviolet range. Thus, some instruments currently available in the art are configured with ultravioletemitting sources, such as the four-laser, 10-color Becton Dickinson LSR II. Further, using a commercially available fluorescence activated cell sorter, such as the FACSVantage™ (Becton Dickinson, San Jose, Calif.), the EPICS® ALTRA™ (Beckman Coulter, Fullerton, Calif.) or the MoFlo® sorter (DakoCytomation, Inc., Carpinteria, Calif.) cell populations can also be sorted into purified fractions.

In one embodiment, once the abnormal cells are identified by flow cytometry as described herein, the cells are sorted and collected for further confirmatory genetic analysis. A desired number of cells is collected using the parameters of the flow cytometer according to established protocols known to the skilled artisan and as described in the art, for example, in Current Protocols in Cytometry (John Wiley & Sons, NY, NY, Eds. J. Paul Robinson, et al.). The cells are collected into one or more drops of collection fluid. In one embodiment, single cells are collected in each small drop of collection fluid. As the cells are collected, the drops containing the desired sorted, purified population of cells (fraction) are deposited into tubes, plates, or onto a solid support. Many distinct populations of cells can be sorted, as defined by immunofluorescent markers as described herein. Accordingly, 1, 2, 3, 4, 5, 6, or more distinct populations (fractions) of cells can be sorted and collected as described herein. In certain embodiments, the sorted cells comprise B cells, T cells, NK cells, plasma cells, stem cells, granulocytes, basophils, or other cells found in the blood.

One advantage of the present invention is that very few cells are needed for analysis to confirm the presence of minimal disease. Thus, in certain embodiments, the number of sorted cells to be analyzed can be about 2000, 1500, 1000, 950, 900, 850, 800, 750, 700, 650, 600, 550, 500, 450, 400, 350, 300, 250, 200 or fewer cells.

Part 3

Monocytes of Control Subjects Show High Uptake of FITC-Aβ by Flow Cytometry

Figure 1C:
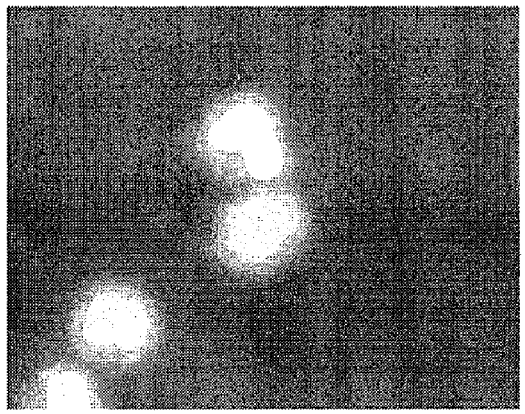
Figure 1C:
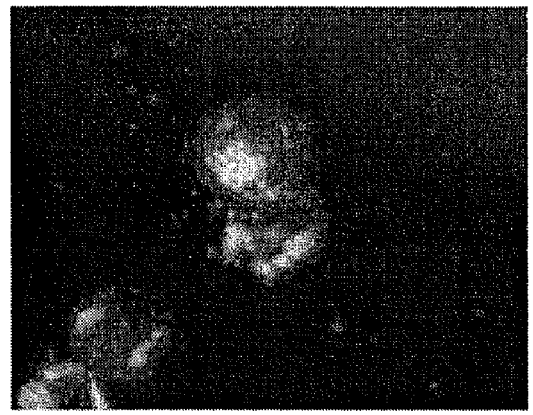
Figure 1C:
Figure 1C:
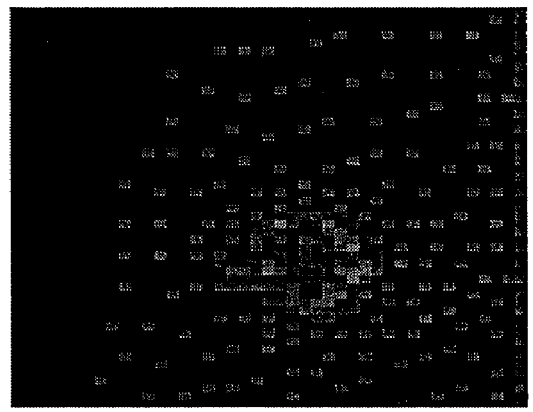

The uptake of FITC-labeled Aβ by CD14-positive monocytes was tested by flow cytometry in samples obtained from 12 AD patients and 10 age-matched normal control subjects. All control monocytes showed an intensive uptake (mean UR uptake $>10^3$ Units). Nine AD monocytes had a low uptake (mean UR uptake $<10^3$ Units) but three had a high uptake (mean UR uptake $>10^3$ Units) (FIG. 1A, P=0.020 by Mann-Whitney t-test). To distinguish intracellular from surface uptake, monocytes, from a control subject and an AD patient were sorted according to the intensity of the FITC-Aβ signal (FIG. 1B). Then sorted monocytes were collected by cytocentrifugation on a slide and prepared for immunofluorescence microscopy: whereas control monocytes displayed intracellular fluorescence, AD monocytes displayed surface staining (FIG. 1C).

Surface uptake does not necessarily lead to effective phagocytosis. To distinguish surface from intracellular uptake, the method of phagocytosis testing was redirected to cytocentrifugation and fluorescence microscopy.

Monocytes of Control Subjects Show a High Intracellular Uptake of FITC-Aβ by Fluorescence Microscopy In the fluorescent antibody test technique, monocytes were incubated with cold Aβ and uptake was measured by indirect fluorescence using anti-Aβ staining. The test was performed in 18 patients and 18 control subjects; the Aβ integrated optical density ("IOD") (calculated as area x density) was measured in the 3 individual monocytes with the largest, second largest, and third largest uptake in each specimen. Significant differences were observed in each category: largest (mean area AD vs. control, 23.8 px vs. 337.4 px), second, largest (mean area AD vs. control, 18.2 px vs. 193.5 px), and third largest uptake (mean area AD vs. control, 12.7 px vs. 117.2 px). The analysis showed significantly higher uptake by control monocytes (P<0.001).

Figure 2A:
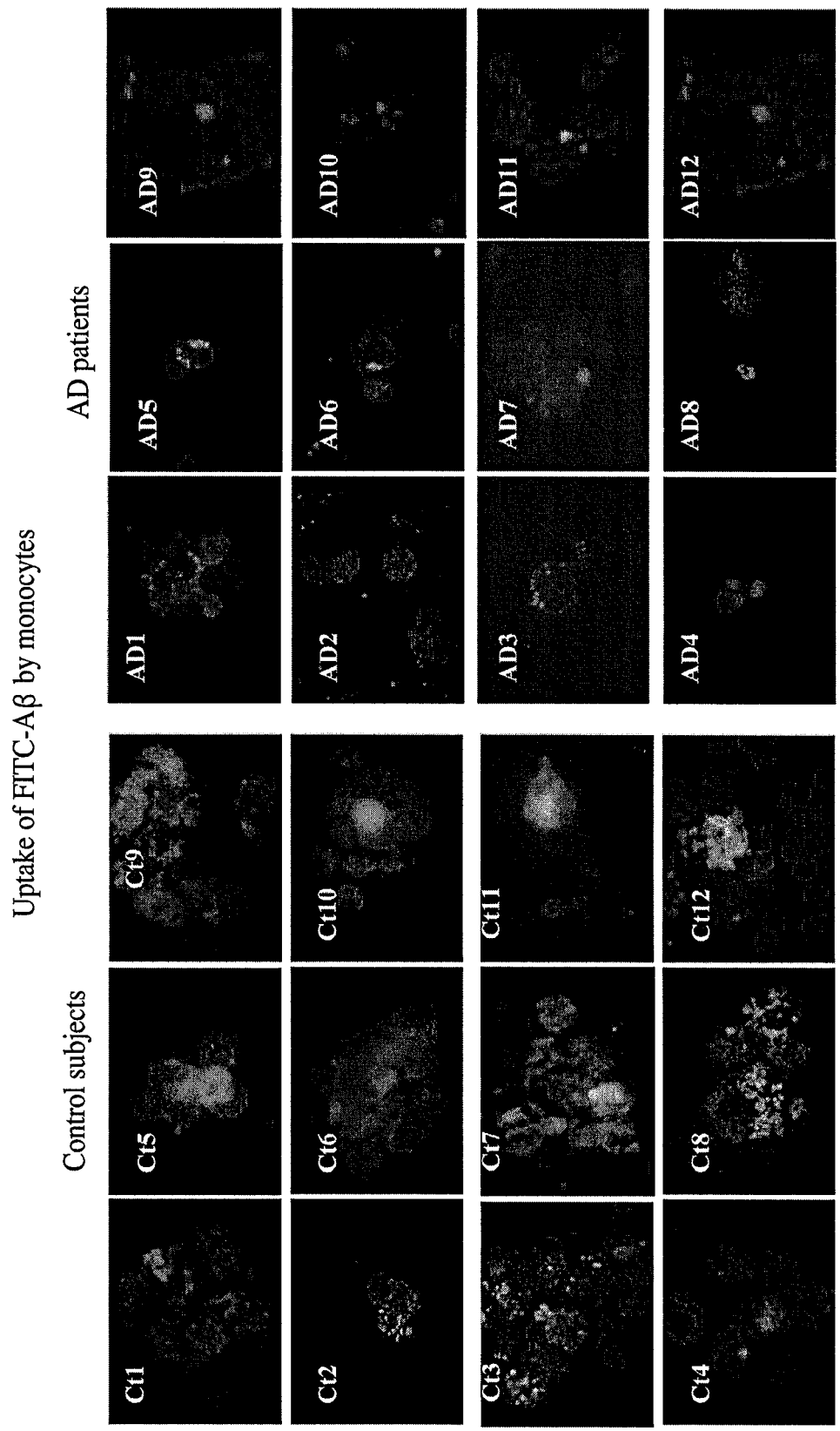
FIG. 2. FITC-Aβ microscopic test: clustering of control monocytes around aggregated Aβ. PBMC's of 12 control subjects and 12 patients were incubated with FITC-Aβ (2 µg/ml) overnight and stained with CD68/ALEXA 555. (A) Uptake of Aβ by monocytes: Photographs of the largest cluster of monocytes with FITC-Aβ in each control and patient cytospin preparation (100× objective of the Olympus microscope and Hamamatsu camera). (B) IOD per monocyte: Five largest monocyte clusters with FITC-Aβ were photographed, fluorescence was scanned by Image Pro and the data were analyzed by ANOVA using a linear model (P=0.001, controls vs. patients).
Figure 2B:
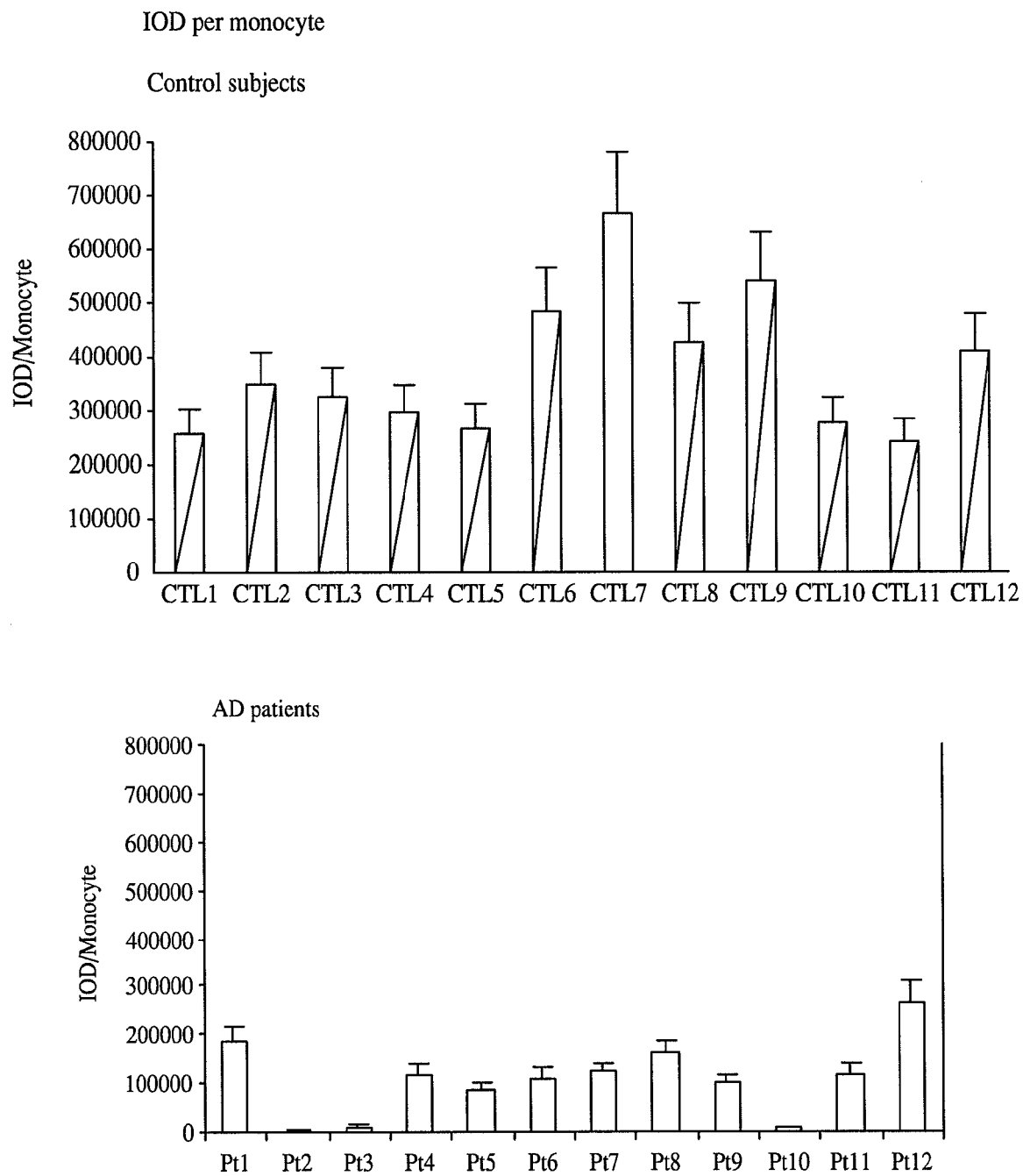

In the FITC-Aβ test, monocytes of 12 controls and 12 patients were examined regarding the Aβ IOD and the pattern of monocyte aggregation. Microscopic examination showed that control monocytes clustered and entrapped large amounts of aggregated FITC-Aβ, whereas AD monocytes showed less clustering and uptake of FITC-Aβ (FIG. 2). The analysis of retained FITC-Aβ showed greater IOD of Aβ per monocyte in control vs. AD preparations (P=0.001).

To clarify the interactions between monocytes and Aβ, cells were stained with antibodies to CD44, a receptor for hyaluronic acid that mediates cell-cell interactions.

Figure 3A:
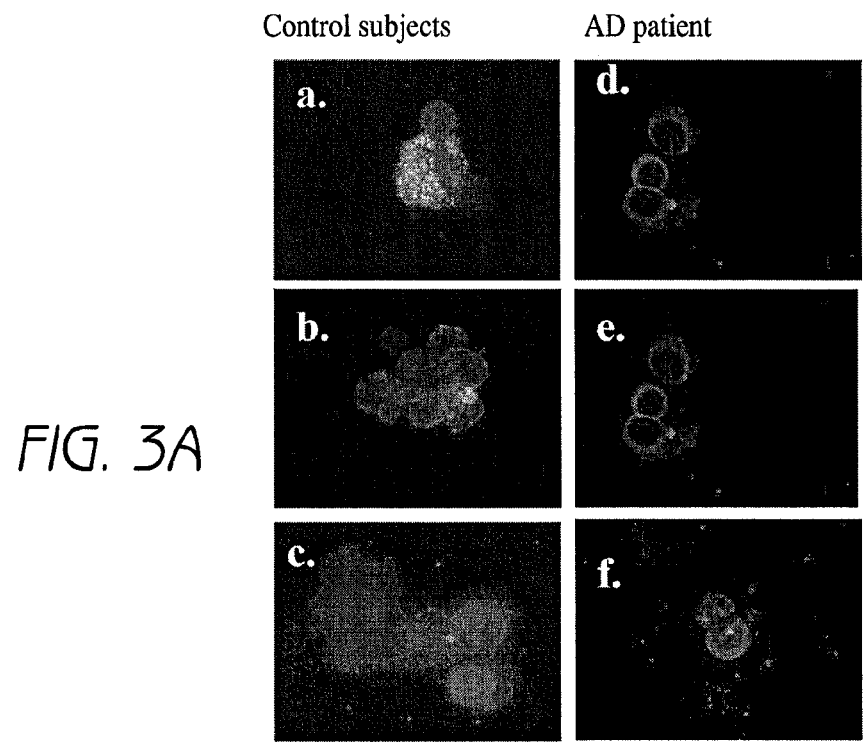
FIG. 3. Expression of CD44 on phagocytic cells. PBMC's of a control subject and a patient were incubated with FITC-Aβ (2 µg/ml) overnight and stained with anti-CD44/ALEXA 555. Note high expression of CD44 on phagocytic cells in control preparation but lack of expression of CD44 on AD cells.
Figure 3B:
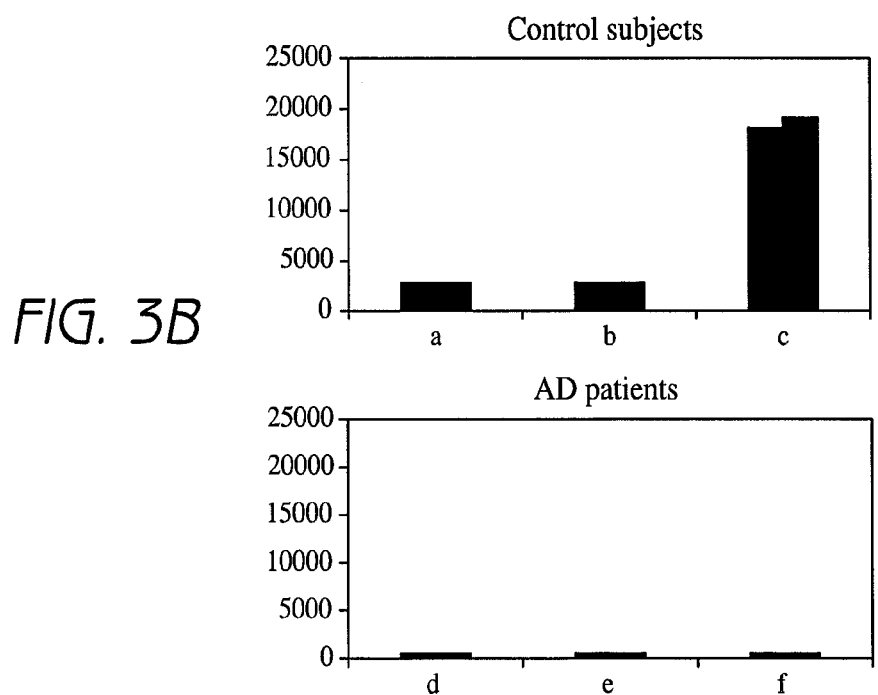
Figure 4A:
FIG. 4 Phagocytosis of FITC-Aβ by control and patient monocytes. PBMC's of 30 control subjects and 30 AD patients were incubated with Aβ (2 mg/ml) overnight, cytospun on a glass slide, stained with anti-CD68, photographed and uptake of FITC-Ab (IOD) was determined by Image-Pro. (A) Uptake of Aβ by monocytes: Photographs of the largest cluster of monocytes with FITC-Aβ in each control and patient cytospin preparation (100× objective of the Olympus microscope and Hamamatsu camera). (B) IOD per monocyte: Five largest monocyte clusters with FITC-Aβ were photographed, fluorescence was scanned by Image Pro and the data were analyzed by ANOVA using a linear model (P=0.001, controls vs. patients). (C) Flow cytometry of FITC-Aβ uptake.
Figure 4A:
Figure 4B:
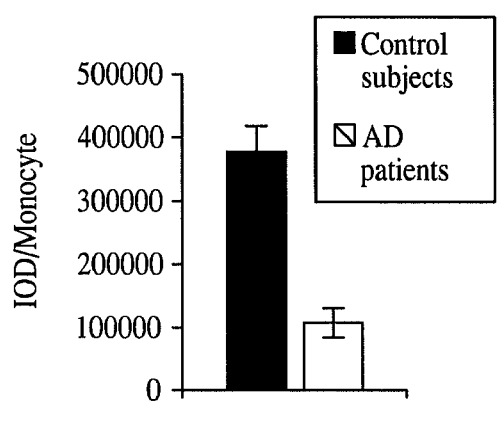
Figure 4C:
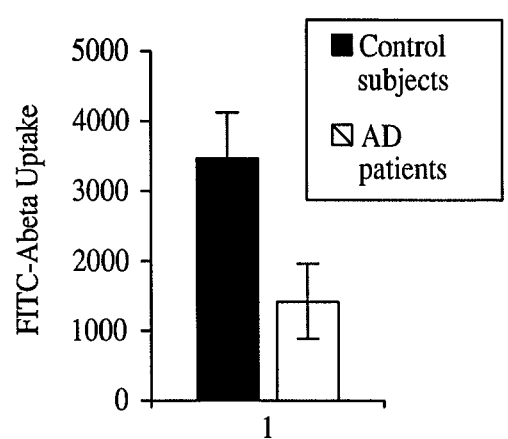
Figure 5A:
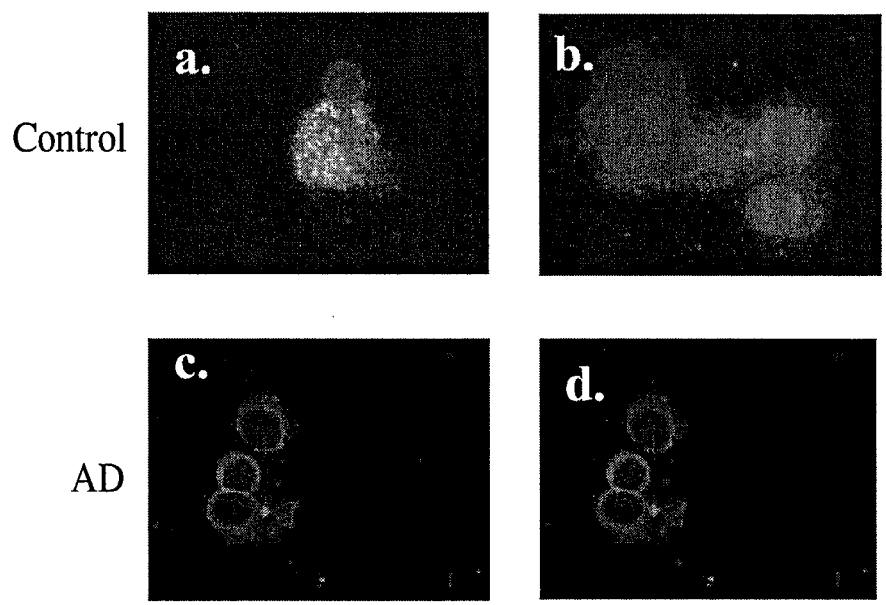
FIG. 5 Expression of CD44 is increased on monocytes of control subjects. PBMC's of a control subject and a patient were incubated with FITC-β (2 µg/ml) overnight, and cytospun, stained with anti-CD44/ALEXA 555, photographed and IOD of CD44 was determined by Image-Pro. Note high expression of CD44 on phagocytic cells in the control preparation (a, b) but lack of expression of CD44 on AD cells (c,d).
Figure 5B:
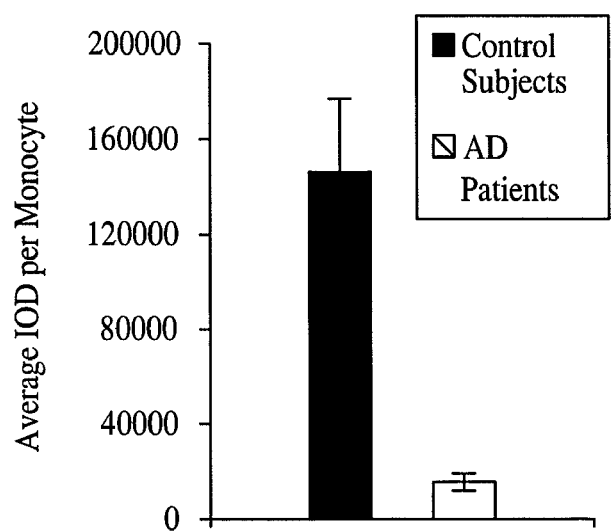
Figure 5C:
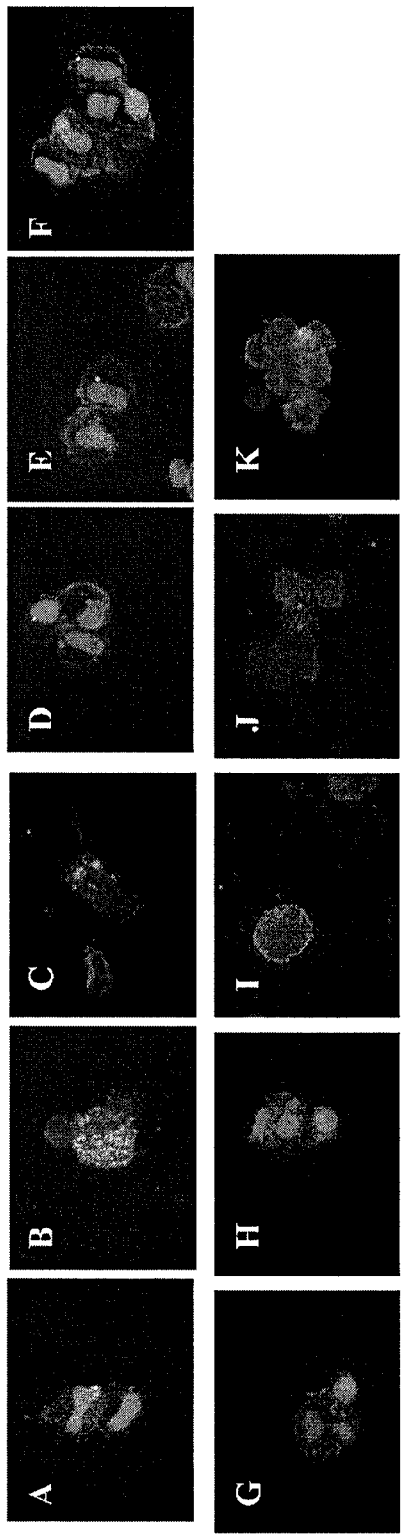
Figure 5C:
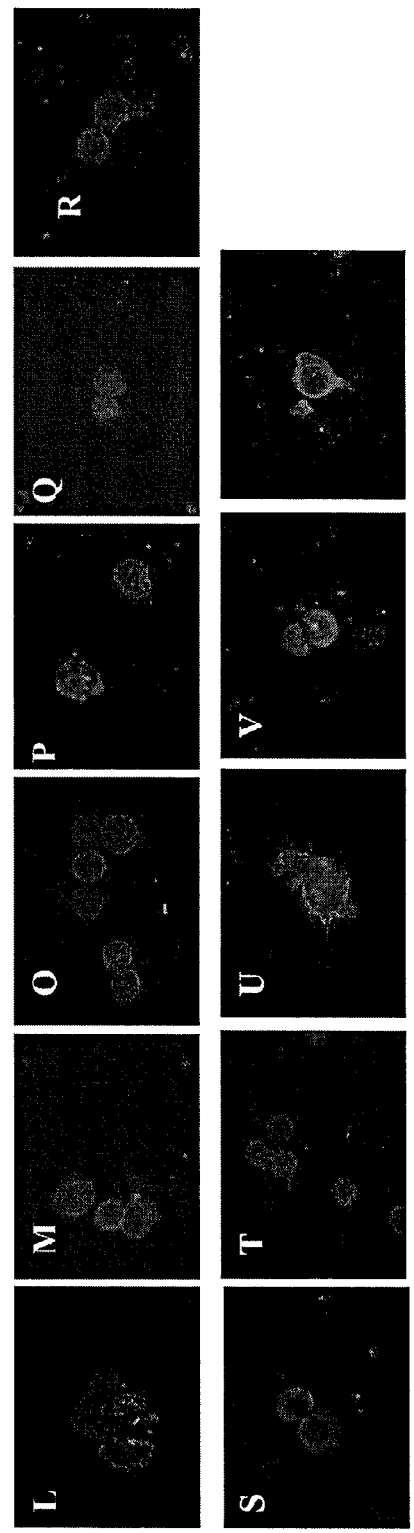

Monocytes of Control Subjects Express CD44 During Aβ Phagocytosis:

After 24h-incubation with FITC-Aβ, monocytes from a control subject displayed abundant CD44, aggregated into clusters, and some cells developed dendrites binding FITC-Aβ. In contrast, the monocytes from AD patients showed scant CD44, small clusters, no dendrites and poor uptake of FITC-Aβ (FIG. 3).

Part 4

Classical biomarkers of AD are based on the stage markers, phosphorylated τ and Aβ, which are a measure of neurodegenerative pathology. In this study, Applicants performed tests relying on Aβ phagocytosis, which are based on immune defects in AD patients.

Applicants found that in all three tests of Aβ phagocytosis, control monocytes demonstrated increased uptake and AD monocytes decreased uptake. The flow cytometric results confounded surface uptake with intracellular phagocytosis and showed false positive results. Of the two immunofluorescent microscopic tests, the FITC-Aβ test was easier to perform. The fluorescent pictures show monocyte clustering in control preparations, high uptake of FITC-Aβ and high expression of CD44; all of these manifestations were numerically decreased but not abolished, in AD preparations. The strategies employed by monocytes to clear Aβ appear to include both high intracellular Aβ uptake and aggregation of Aβ by a cluster of surrounding monocytes. In addition, the expression of dendrites on monocytes reflects their maturation into macrophages and dendritic cells. Applicants have rarely seen dendrites on the monocytes of AD patients.

Applicants do not know precisely at which stage of the disease the patients develop these defects of Aβ phagocytosis. If as hypothesized, defective phagocytosis is a link in the immunopathogenesis of AD, then these tests should serve as an early biomarker. We have, however, not excluded the possibility that the defects result from the disease and, therefore represent a late manifestation. Our testing of patients with minor cognitive impairment was likely to shed light on this question. Notwithstanding this question or causality or manifestation, our functional approach to AD biomarkers does not rely on identification of single proteins but takes into consideration the complex process of monocyte/macrophage maturation and phagocytosis. In contrast, the proteomic technique for detection of biomarkers in CSF has identified 136 CSF proteins unique to AD but encompassing disparate functions, which could be related to various, possibly secondary, mechanisms of the disease, such as inflammation, blood-brain barrier damage and apoptosis. It is desirable to compare the biomarkers reflecting innate immunity or proteomic differences at an early stage of the disease. We have undertaken studies to elucidate the molecular mechanisms responsible for defective phagocytosis. We have recently shown that after Aβ stimulation, RNA for the glycosylating enzyme MGAT3 is not properly transcribed in AD patients' monocytes and macrophages.

EXAMPLES

Reagents and Antibodies:

Aβ (1-42) ("cold Aβ") (California Peptide Research, Napa, Calif.), Aβ (1-42) conjugated with fluorescein isothiocyanate ("FITC-Aβ") (AnaSpec, San Jose, Calif.); mouse anti-(human) CD68 (KP-1) (DAKO, Carpinteria, Calif.); rabbit anti-Aβ (specific for 6 amino acid sequence from the C-terminal of human amyloid-beta 1-42) (Chemicon, Temecula, Calif.); mouse anti-human HLA DR (Becton Dickinson, Pharmingen, San Diego, Calif.); anti-CD14-PE (BD Pharmingen, San Diego, Calif.); tetramethylrhodamine-phalloidin (Sigma, St. Louis, Mo.); mouse monoclonal anti-human CD44H (R&D Systems, Minneapolis, Minn.); Alexa488- and Alexa594-conjugated anti-mouse and anti-rabbit IgG (Molecular Probes, Eugene, Oreg.).

Patients with Alzheimer Disease and Control Subjects:

We investigated 38 ambulatory patients (mean age 77.2 years, mean mini mental score examination (MMSE) 21.7) with a diagnosis of probable AD established by the NINCDS/ADRDA criteria (McKhann G et al. 1984. *Neurology* 34:939-944) regarding phagocytosis of Aβ by three techniques (10 patients by flow cytometry, 18 patients by indirect fluorescence and 10 patients by FITC-Aβ test) under a protocol approved by UCLA Institutional Review Board. We tested in parallel 39 control subjects (mean age 69.4+9.4 years) (10 by flow cytometry, 17 by indirect fluorescence and 12 by FITC-Aβ test) whom we recruited from UCLA personnel and families of patients.

Floss Cytometiy of Aβ Phagocytosis and Apoptosis

PBMC's were isolated from venous blood by the Ficoll-Hypaque gradient centrifugation technique as described (Fiala et al. 2005. *J. Alzheimers Dis* 7:221-232; discussion 255-262). For flow cytometry, 500,000 PBMC's were incubated overnight in RPMI medium with 10% autologous serum and FITC-Aβ (2 μg/ml), stained with anti-CD14-PE, and examined using BD FACScan Analytic Flow cytometer. The data were gated on monocytes, which were selected as the cells with greater forward scatter and side scatter voltages than lymphocytes. The amplification gain and voltages were adjusted to comprise about 100%, unstained cells in LL, about 100% FITC-stined cells in LR, and about 100% PE-stained cells in UL. Mean UR fluorescence was analyzedl. Control and AD PBMC's were sorted using BD FACSVantageSE sorting flow cytometer according to the FITC-Aβ signal intensity.

Fluorescence Microscopy of Phagocytosis Using (a) Indirect Fluorescence Antibody Technique, or (b) FITC-Aβ

For immunofluorescence microscopy, 50,000 PBMC's were incubated in Iscove's modified Dulbecco's medium (GIBCO) with 10% autologous serum, penicillin (100 U/ml)-streptomycin (100 μg/ml)-fungizone (2.5 μg/ml), and either cold Aβ (2 μg/ml) in the indirect fluorescence technique, or FITC-Aβ (2 μg/ml) in the FITC-Aβ test. After overnight incubation, PBMC's were collected by cytocentrifugation in a double cytology funnel (Fisher Scientific) at 500 RPM for 10 min (Cytospin 2, Thermo Shandon) on a glass slide. In the indirect fluorescence technique, the cells were stained using anti-Aβ/anti-rabbit ALEXA 488 and anti-CD68/anti-mouse ALEXA 594 and DAPI (1:300); in the FITC-Aβ test, using anti-CD68/anti-mouse ALEXA 594 and DAPI. The cytospun preparations were examined using the 40x objective of the Olympus Bmax fluorescence microscope by scanning a midline vertical strip of the spot with cytospun cells for aggregated monocytes with FITC-Aβ. After locating the five largest aggregations (large aggregations were noticeable in control specimens but only small aggregations or single cells with FITC-Aβ in AD specimens (see FIG. 2)), 40x raw pictures were obtained using the Hamamatsu digital camera for each fluorophore (red, green and blue) (shown in figures as medium grey, light grey and dark grey), single and overlay pictures were created using the RGB tuner and saved. The pictures were analyzed using the Image Pro software (Media Cybernetics, Inc., Bethesda, Md.) regarding IOD(mean) of FITC fluourescence. Any FITC-Aβ artifacts (FITC-Aβ without monocytes) were eliminated from analysis. The number of nuclei was determined for each DAPI-stained picture in each monocyte aggregation and the FITC-Aβ IOD per monocyte was determined by dividing the sum of FITC-Aβ IOD's in 5 pictures by the total number of nuclei.

Statistical Analysis

Statistical testing was performed by the t-test and Mann-Whitney U test (FIG. 1, fluorescent antibody test, apoptosis test) or repeated measures analysis of variance (FIG. 2) using the statistical software SPSS, Version 10.0 (SPSS, Chicago).

Alzheimer's Kit

Reagents and Labware Provided for an 8 Well Chamber Slide (One Embodiment of the Disclosed Kit)
  HBSS
  PBS
  Iscove's Modified Dulbecco's Medium (cell culture medium from Sigma-Aldrich)
  PENSTREP/FUNGIZONE antifungal agents
  Histopaque-1077
  Paraformaldehyde
  FITC-Amyloid-β
  Phalloidin-tetramethylrhodamine
  LYSOTRACKER fluorescent acidotropic probes
  Antifade
  Heparin
  8 well chamber slide
Reagents and Labware not Provided (in the Above Embodiment)
  Pipets and tips
  Blood collection tubes
  15 mL Centrifugation tubes (Becton Dickinson Labware)
  100 mm culture dish
  DURASEAL stretch film In addition, the disclosed kit is designed to utilize about 5 mL to 10 mL of EDTA-anticoagulated blood and 10 mL of coagulated blood. Of course in other embodiments, other samples may be utilized.

Methods for Isolating and Seeding Macrophages
  1. In 15 mL centrifuge tubes, place 4 mL of Histopaque-1077.
  2. Warm up, to room temperature, the Histopaque-1077, the EDTA anticoagulated blood and the PBS.
  3. Dilute EDTA anticoagulated blood with equal volume of 1× PBS.
  4. Place 10 mL of diluted blood on top of the 4 mL Ficoll-Hypaque. Pipet blood slowly to avoid mixing with Ficoll-Hypaque.
  5. Centrifuge at 2300 rpm for 20 minutes at 4° C. (rotor radius 15 cm to bottom of the bucket).

6. Carefully remove and discard the clear fluid (plasma) until turbid band of mononuclear cells is reached.
7. Collect the peripheral blood mononuclear cells (PBMC), corresponding to the turbid layer, without removing the Ficoll-Hypaque (clear layer). Place the PBMC in a new 15 mL centrifuge tube and dilute the PBMC 1:3 with HBSS.
8. Centrifuge at 2300 rpm for 10 minutes at 4° C.
9. In the meantime, centrifuge the clotted blood at 1000 rpm for 5 minutes at 4° C. to obtain the serum (supernatant). Transfer the serum to a new tube.
10. Resuspend cells, from step 8, in 5 mL Iscove's medium with PENSTEP/FUNGIZONE antifungal agents, 10% autologous serum and heparin.
11. Perform cell counting and adjust concentration between 125 000 cell and 250 000 cells per mL.
12. In each of the 8 well chamber slide, seed between 50 000 and 100 000 cells per well in 0.4 mL of media.
13. Place the 8 well chamber slide into a 100 mm culture dish. Seal the edge of the dish with stretch film and incubate at 37° C. in a humidified $CO_2$ incubator for 7 to 14 days until macrophages become differentiated. Macrophages remain viable for 15 days.
14. Pre-treat the macrophages overnight with 0.1 μg/ml or 1 μg/mL of the product to test. A well is left untreated for control.
15. Acid 10 μL of FITC-amyloid-β in each well (final concentration of 2.5 μg/mL).
16. Incubate at 37° C. in a humidified $CO_2$ incubator overnight.
17. Add 4 μL of lysotracker in each well.
18. Incubate for 30 minutes at 37° C. in a humidified $CO_2$ incubator.
19. Remove the media and wash with 1.0 mL of PBS.
20. Fix cells by adding 100 μL of 3.7% paraformaldehyde for 20 minutes.
21. Wash with 1.0 mL of PBS.
22. Repeat wash if desired.
23. Dilute the phalloidin-tetramethylrhodamine 1:200 with PBS.
24. Stain cells by adding 100 μL of diluted phalloidin-tetramethylrhodamine for 20 minutes.
25. Wash with 1.0 ml of PBS.
26. Repeat wash if desired.
27. Add 0.2 mL of Antifade.
28. Observe results with fluorescence and/or confocal microscopy.

Based on Applicants results shown in FIGS. 1 and 2, we expect that the macrophages from Alzheimer patients' will transport significantly less Aβ into intracellular locations. In contrast, we expect the macrophages from control subjects' will transport significant amounts of Aβ into intracellular locations, such as endosomes and lysosomes. Confocal microscopy can be used to determine the subcellular localization of the transported Aβ.

Analysis of data We investigated FITC-Ab clearance by monocytes in culture using cytospin centrifugation and fluorescence microscopy. Control monocytes, which were exposed to Ab for 24 to 48h, increased in size, some with a display of dendrites on the surface, and formed multicellular aggregates surrounding globules of Ab. These monocytes showed intensive uptake of FITC-Ab into an intracellular site. AD monocytes showed less prominent transformation and uptake of FITC-Ab, which was limited to cell surface, as previously shown with AD macrophages {Fiala, 2007 #2634} (FIG. 1A). Control monocytes immobilized significantly more FITC-Ab in comparison to AD monocytes, as demonstrated by higher integrated optical density (IOD) of FITC-Ab (FIG. 1A).

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

---

What is claimed is:

1. A method for diagnosing Alzheimer's disease in a patient, comprising:
    providing a test cell sample from the patient, wherein the test cell sample comprises peripheral blood mononuclear cells;
    exposing the test cell sample to labeled amyloid beta polypeptide;
    determining a level of the labeled amyloid beta polypeptide uptake by the test cell sample; and
    determining a level of expression of CD44 in the test cell sample,
    wherein a lower level of both labeled amyloid beta polypeptide uptake and CD44 expression in the test cell sample compared to a control cell sample is indicative of Alzheimer's disease.

2. The method of claim 1, wherein the labeled amyloid beta polypeptide is selected from the group consisting of a full length amyloid beta protein and a fragment thereof.

3. The method of claim 2, wherein the fragment is a 1-40 or 1-42 amino acid fragment, SEQ ID No: 1 or SEQ ID No: 2.

4. The method of claim 1, wherein the labeled amyloid beta polypeptide is fluorescently labeled.

5. The method of claim 4, wherein the fluorescently labeled amyloid beta polypeptide is labeled with FITC.

6. The method of claim 1, wherein the labeled amyloid beta polypeptide is radiolabeled.

7. The method of claim 1, wherein the labeled amyloid beta polypeptide is chromatogenically labeled.

8. The method of claim 1, wherein the level of labeled amyloid beta polypeptide uptake is determined by fluorescence microscopy imaging.

9. The method of claim 1, wherein the level of labeled amyloid beta polypeptide uptake is determined by flow cytometry.

10. The method of claim 1, wherein the level of labeled amyloid beta polypeptide uptake is determined by radioassay.

11. The method of claim 1, wherein the level of labeled amyloid beta polypeptide uptake is determined by a chromogenic or absorbance based assay.

12. The method of claim 1, further comprising a washing step after exposing the test cell sample to a labeled amyloid beta polypeptide.

13. The method of claim 12, wherein the washing step comprises exposing the test cell sample to PBS.

14. The method of claim 1, wherein exposing the test cell sample to labeled amyloid beta polypeptide further comprises adding a blocking agent.

15. The method of claim 14, wherein the blocking agent is bovine serum albumin.

16. A method of diagnosing Alzheimer's disease in a subject comprising:
    providing peripheral blood monocytes from the subject;
    exposing the peripheral blood monocytes to amyloid beta polypeptide; and
    determining a level of CD44 expression, wherein a lower level of CD44 expression in the peripheral blood monocytes compared to a control cell sample is indicative of Alzheimer's disease.

* * * * *